United States Patent

Krause et al.

[11] Patent Number: 5,065,760
[45] Date of Patent: Nov. 19, 1991

[54] CABLE GUIDE FOR A NUCLEAR MAGNETIC RESONANCE TOMOGRAPHY APPARATUS

[75] Inventors: Norbert Krause, Heroldsbach; Wilhelm Hanke, Rueckersdorf; Juergen Ruhl, Erlangen, all of Fed. Rep. of Germany

[73] Assignee: Siemens Aktiengesellschaft, Munich, Fed. Rep. of Germany

[21] Appl. No.: 592,293

[22] Filed: Oct. 3, 1990

[30] Foreign Application Priority Data

Oct. 20, 1989 [DE] Fed. Rep. of Germany ....... 3935082

[51] Int. Cl.$^5$ ............................................. A61B 5/055
[52] U.S. Cl. .............................. 128/653.5; 128/653.2; 324/318
[58] Field of Search ..................... 128/653 A, 653 SC; 324/318, 322

[56] References Cited

U.S. PATENT DOCUMENTS 4,972,852 11/1990 Koob et al. ..................... 128/653 A

FOREIGN PATENT DOCUMENTS 3327731 2/1985 Fed. Rep. of Germany .

Primary Examiner—Ruth S. Smith

[57] ABSTRACT

A cable guide for use in a nuclear magnetic resonance tomography apparatus is provided for cable for making electrical connections between devices secured to a patient bed and devices disposed outside of the examination space. The cable guide is a grounded, electrical cable channel disposed beneath the patient bed and above the lower sub-antenna of a whole-body antenna and above at least one wall of the examination space. The cable channel has a V-shape, and is rounded at an edge facing the examination space, this edge projecting beyond the height of the lower sub-antenna. The cable guide substantially protects the cable against coupling with other components. The examination space remains free of built-in units.

17 Claims, 3 Drawing Sheets

CABLE GUIDE FOR A NUCLEAR MAGNETIC RESONANCE TOMOGRAPHY APPARATUS

BACKGROUND OF THE INVENTION

1. Field of the Invention

The present invention is directed to a cable guide for a nuclear magnetic resonance tomography apparatus of the type having a magnet with an opening serving as the examination space with an inside wall on which a whole-body antenna, azimuthally divided into a plurality of sub-antennas, is attached, and into which a patient bed can be introduced.

2. Description of the Prior Art

There is often a need in nuclear magnetic resonance tomography devices to conduct cables from devices arranged at the patient bed to devices disposed outside of the examination space. Devices known as local coils, for example, are often used and are attached as close as possible to the examination region in which the patient is disposed. The local coils are adapted in shape and size to the body part to be imaged. The radio frequency pulses needed to excite the nuclear spins are transmitted by an antenna known as a whole-body antenna, and reception of the nuclear magnetic resonance signals ensues with the local coil. A better signal-to-noise ratio is achieved because the reception region is limited to the examination region of interest. The local coils are secured at the patient bed, or to the patient, while the bed is entered into and withdrawn from the examination space.

In standard nuclear magnetic resonance tomography devices, the nuclear magnetic resonance signals received by the local coil are supplied via a RF cable to a pre-amplifier located outside of the magnet which generates the fundamental field. The local coil, by contrast, is situated within the whole-body antenna, preferably in the immediate proximity of the antenna center because the field homogeneity is best at that location.

In addition to the RF cable for the local coil, further lines to the patient bed are needed in many instances, for example for transmitting control signals for the local coil and for transmitting ECG and respiratory signals of the patient for triggering the imaging.

Problems occur due to cables which must be conducted out of the center of the whole-body antenna when the patient bed is introduced into the opening in the center of the magnet. High electromagnetic fields are present in the whole-body antenna during the transmission phase. Coupling between the cables and the antenna, and thus an RF power flow in the exterior of the cable shielding arise due to skin-effect waves. This can cause considerable disturbances both in the picture quality and in the electronic components. Coupling of the antenna field to the lines ensues magnetically (inductively) and electrically (capacitively).

The magnetic coupling can be minimized by avoiding the formation of loops by the lines inside the whole-body antenna. The electrical coupling can be minimized by conducting the cables to the exterior from the center of the whole-body antenna in a defined fashion in zones of low electrical field strength of the whole-body antenna.

In systems using a linearly polarized antenna, such zones are found in the central cross-sectional plane of the antenna, as well as in the proximity of the antenna shielding foil centrally between the antenna halves.

In systems using a circularly polarized antenna, zones of low electrical field strength are also found in the central cross-sectional plane of the antenna.

In known systems, this zone is used for cable guidance by disposing an electrically shielding cable channel at that location in the form of a metallic profile having a U-shaped cross-section. In such known arrangements, the cable channel thus is disposed above the patient bed. Connection between the cable channel and the patient bed is produced using carriers secured to the patient bed. These carriers, however, cause certain restrictions in the bearing comfort of the patient, because they partially restrict the examination space, which is already designed as tightly as possible for reasons of economic feasibility and RF fields.

German Gebrauchsmuster 84 13 651 discloses a patient bed having a plug mechanism for the connection of a cable to a signal transmission means. This cable is rigidly secured to the patient bed and leads to a stationary apparatus part via a loop in order to enable longitudinal displacement of the patient bed.

German Gebrauchsmuster 89 09 245 also discloses cables leading from a stationary apparatus part to plug mechanisms, which are provided at a side of a patient support table. These cables are conducted along the side of the patient support table, and are surrounded by a cable guide formed by an articulated cladding having a rectangular cross section.

German OS 33 27 731 discloses means for acquiring an ECG signal in a nuclear magnetic resonance tomography apparatus. The connecting cable between the ECG electrodes and the ECG processing means includes cable shielding electrically connected so as to be at the potential of the RF shielding of the tomography apparatus.

SUMMARY OF THE INVENTION

It is an object of the present invention to provide a cable guide for use in a nuclear magnetic resonance tomography apparatus which permits the examination space to remain free of intrusive components.

The above object is achieved in accordance with the principles of the present invention in a magnetic resonance tomography apparatus having a cable channel arranged beneath the patient bed, and above the lower sub-antenna and at a wall of the examination space.

Given a linearly polarizing whole-body antenna wherein respective sub-antennas are arranged above and below the patient bed, the cable channel preferably has a V-shape and is rounded at an edge facing the examination space, this edge projecting beyond the height of the lower sub-antenna.

Given a circularly polarizing whole-body antenna, wherein at least at one sub-antenna is disposed beneath the patient bed, the cable channel preferably has approximately a U-shape, having edges rounded in an outward direction, these edges projecting beyond the height of the neighboring sub-antennas.

By arranging the cable channel beneath the patient support, the cables from the patient can be conducted in a downward direction without the presence of any intrusive built-in units. Although the cable channel is not in the zones of the lowest field strength, a good shielding is nonetheless insured due to the special shape of the channel.

DESCRIPTION OF THE PREFERRED EMBODIMENTS

Figure 1:
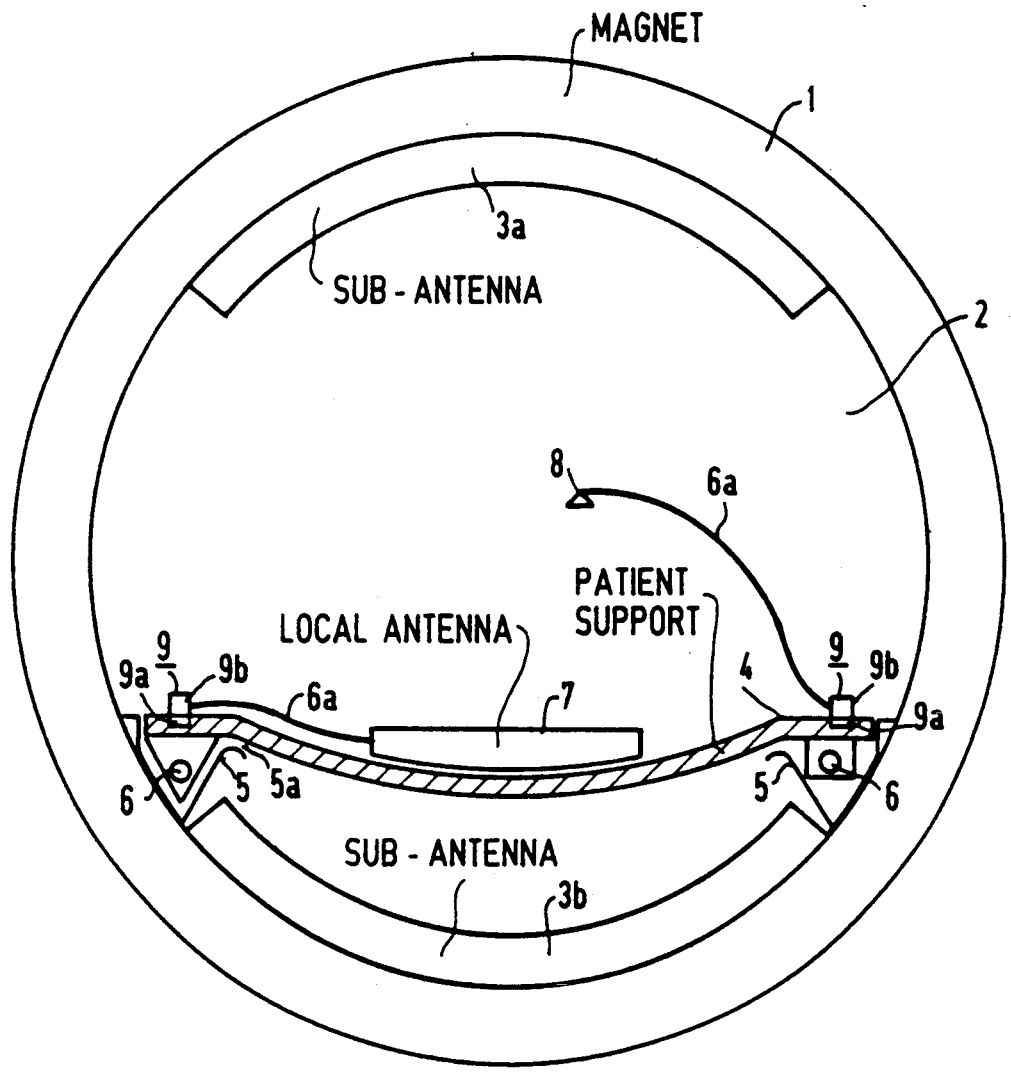
FIG. 1 is an end elevational view of the relevant portions of a nuclear magnetic resonance tomography apparatus constructed in accordance with the principles of the present invention.

A nuclear magnetic resonance tomography apparatus having a linearly polarizing whole-body antenna is shown in FIG. 1, with only the components necessary for an explanation of the invention being present for clarity. The apparatus includes a superconducting magnet 1, schematically shown in FIG. 1, having a cylindrical central opening 2. A whole-body antenna is present, consisting of two sub-antennas 3a and 3b attached to the walls of the opening 2, which defines an examination region. Radio frequency pulses are transmitted via this whole-body antenna, and are also received by this antenna under certain circumstances, if a local coil is not used for this purpose. The RF field of the whole-body antenna is as uniform as possible over the examination region defined by the opening 2. The patient is moved into the opening 2 of the magnet 1 on a patient support 4. The surface of the patient support 4 is disposed so that the patient comes to lie optimally centrally within the magnet 1, i.e., the patient support is disposed beneath the center of the magnet 1.

In the exemplary embodiment of FIG. 1, a local coil 7, disposed optimally close to the body surface of a patient, is arranged on the patient support 4. A group of ECG electrodes 8, by means of which an ECG of the patient can be obtained and which can be used to trigger image acquisition, is provided. The signals from the group of ECG electrodes 8 and from the local coil 7 are respectively conducted out of the examination space 2 via cables 6. Under certain conditions, control signals for the local coil 7 may also be transmitted via the cables 6, for example, for tuning the local coil 7.

Cable channels 5 are provided in the examination space 2 at both sides of and under the patient bed 4, for guiding the cables 6. A left cable channel 5 in FIG. 1 serves, for example, for the acceptance of a RF cable, and the right cable channel 5 serves, for example, for accepting the remaining cables 6. The cable channels 5 are attached directly to the exterior wall of the opening 2 above the sub-antenna 3b. The channels 5 have a V-shape, with the inside edge of each channel 5 being bent to form a rounded edge. The cable channels 5 are grounded by connection to a foil (not shown) surrounding the examination space 2.

As noted above, the cable channels 5 in this embodiment do not lie in the zone of minimum field strength of the whole-body antenna 3. Due to the special shape of the cable channels 5, however, the cables 6 nonetheless are contained in a space having extremely low field strength. The electromagnetic field in the cable channels 5 is predominantly generated by the lower, closer sub-antenna 3b, so that shielding in this direction is the most necessary. This is achieved by extending the cable channel 5 beyond the height of the sub-antenna 3b. Due to the rounding at the inside edges 5a of the channels 5, parasitic stray fields in the interior of the cable channel 5, caused by compensation currents at the edges, are avoided.

Connection between the local coil 7, or the ECG electrode 8, and the cables 6 in the cable channels 5 ensues at both sides via plug connectors 9. Lower plug parts 9a are provided for this purpose at the edge of the patient bed 4, with plugs 9b of the local coil 7, or of the ECG electrode 8, being plugged therein. The connecting lines 6a between the local coil 7, or the group of ECG electrodes 8, and the plugs 9, extend transversely to the sockets 9a over the shortest possible path.

Figure 2:
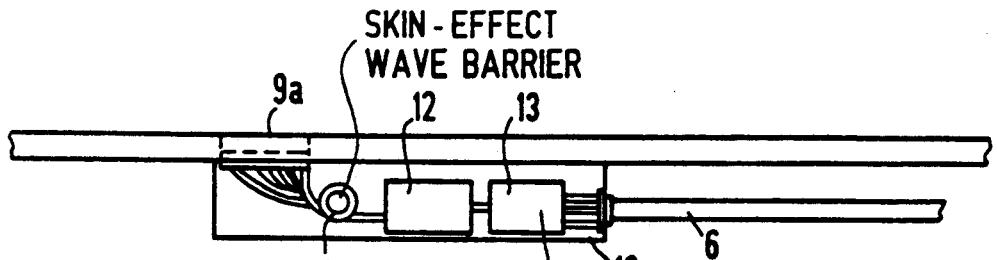
FIGS. 2 and 3 are side views, showing electrical components in schematic illustration, of sockets for connecting the cable which may be used in the embodiments of FIGS. 1 or 5.
Figure 3:
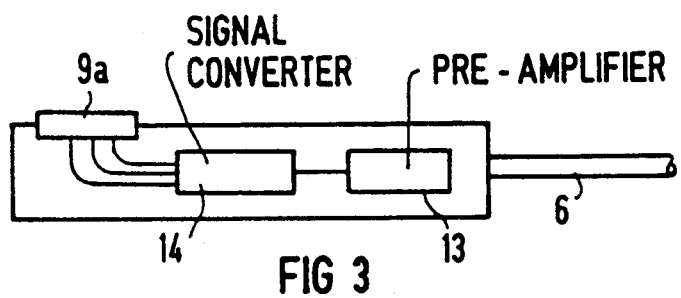

As can be seen in FIGS. 2 and 3, the sockets 9a are part of a connector unit 10. In order that the connection between the sockets 9a and the local coil 7 or the ECG electrode 8 be produced over the shortest path, these conductor units are displaceable in the longitudinal direction of the patient support 4. The connector units 10 are designed so as to lie within the respective cable channel 5. FIG. 2 shows a connector unit 10 for the cable 6 for the transmission of RF signals. The lines leading from the lower plug part 9a are conducted via a skin effect wave barrier 11, a directional coupler 12, and a pre-amplifier 13 to the cable 6, which is then conducted out of the magnet via the cable channel 5.

Figure 4:
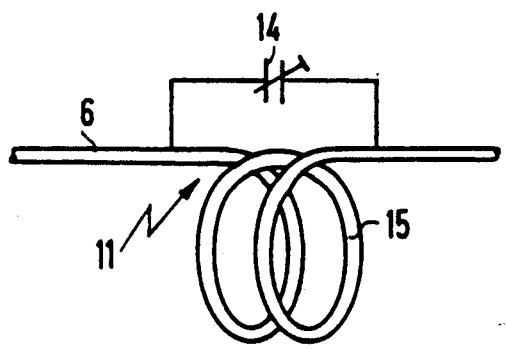
FIG. 4 is a schematic illustration of a skin effect wave barrier which can be used in any of the embodiments of the invention.

As shown in FIG. 4, the skin effect wave barrier 11 can be executed as a parallel resonance circuit consisting of a coil 15, formed by winding the cable 6, and a capacitor 14 bridging this coil and connected to the shielding of the cable 6. This prevents forwarding of RF power along the cable shielding which can be coupled, given unfavorable positioning between the local coil 7, or the ECG electrode 8, and the plug connectors 9.

For tuning the local coil 7, RF power is coupled into the cable 6 to the local coil 7 via the directional coupler 12 and the reflected power is evaluated and minimized via the reception branch. An increase in the signal-to-noise ratio is achieved by the pre-amplifier in the connector unit 10, because the influence of the cable attenuation can be diminished by placing this component close to the local coil 7.

FIG. 3 shows a connector unit for other signals, as an example. The signals obtained from a signal pick-up may be first converted by a signal converter 14 (for example, optical if the signals incoming to the plug part 9a are optical signals, these signals are converted into electrical signals) and may then be amplified using a pre-amplifier 13.

Figure 5:
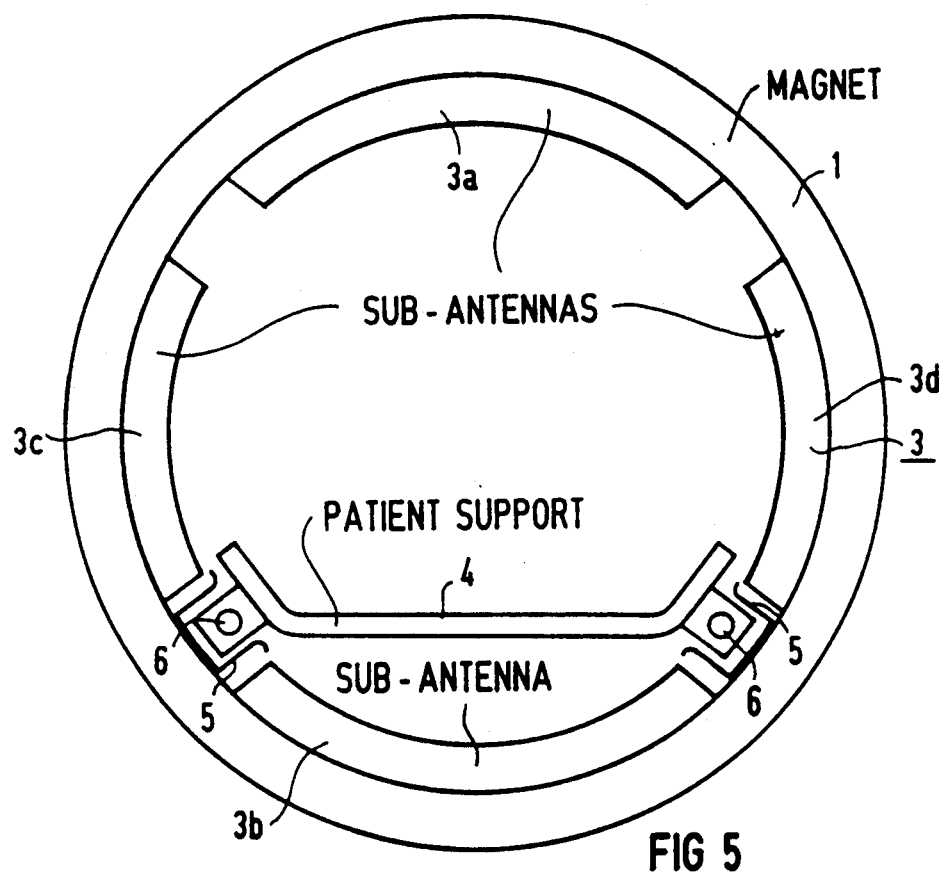
FIG. 5 is an end elevational view of a nuclear magnetic resonance tomography apparatus showing a further embodiment of the invention.

An exemplary embodiment for a cable guide for a nuclear magnetic resonance apparatus using a circularly polarizing whole-body antenna is shown in FIG. 5. In this embodiment, the antenna includes four sub-antennas 3a, 3b, 3c and 3d, uniformly distributed over the circumference of the interior of the magnet 1, with the sub-antenna 3b being disposed beneath the patient support 4. The cable channels 5 are again arranged beneath the patient support 4, and are disposed between two neighboring sub-antennas 3b and 3c, and between 3b and 3d. In this embodiment, the electromagnetic field produced by the sub-antennas 3b and 3c, and by 3b and 3d, is substantially uniform, so that the cable channels 5 have a U-shape which is open toward the center of the examination space defined by the opening 2, which is more favorable for this type of field. As in the case of the V-shape of FIG. 1, the outside edges are rounded to maintain the stray fields caused by compensating currents at the edges away from the interior of the cable channels 5. Otherwise, the structure of the cable guides corresponds to that already described in connection with FIG. 1.

Figure 6:
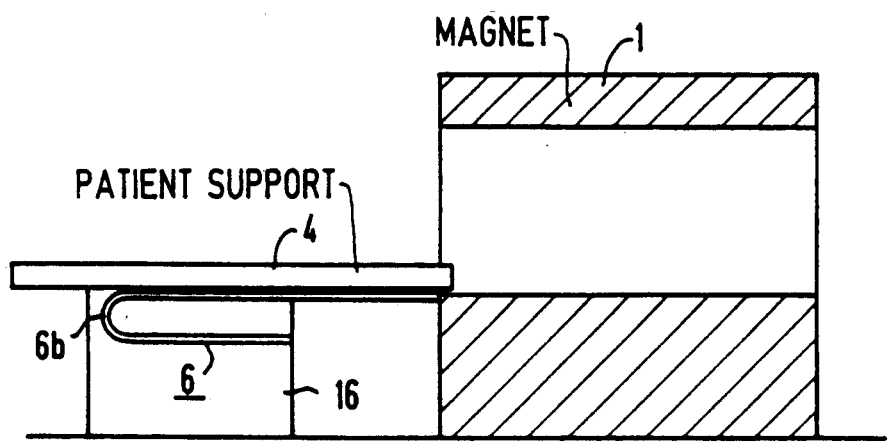
FIG. 6 is a side view of relevant components of a nuclear magnetic resonance tomography apparatus incorporating the invention.

For cables 6 which are connected to a stationary connection outside the examination region, and which are to be introduced into and withdrawn from the examination region together with the patient bed 4, a guide which compensates the cable length outside of the examination region must be present. As schematically shown, for example, in FIG. 6, the cables 6 may be guided for this purpose in a loop 6b inside a column 16 which carries the patient bed 4. The loop 6b is correspondingly shortened when the patient bed 4 is introduced into the interior of the magnet 1.

Coupling influences are substantially avoided with the arrangement described herein due to the cable guidance in a shielded space. The uniformity of the RF field is minimally influenced by the arrangement of the cable channel. The available examination space is in no way restricted, and no intrusive cables lie on the patient support. The local coil 7 and the electrodes 8 are simple to attach.

Although modifications and changes may be suggested by those skilled in the art, it is the intention of the inventors to embody within the patent warranted hereon all changes and modifications as reasonably and properly come within the scope of their contribution to the art.

We claim as our invention:

1. In a nuclear magnetic resonance tomography apparatus having a magnet with a central opening defining an examination space and having a patient support movable into said examination space, said opening having a wall on which a whole-body antenna divided azimuthally into a plurality of sub-antennas for generating a polarized field is attached, said sub-antennas including a lower sub-antenna disposed beneath said patient support when said patient support is in said examination space, said patient support having a plurality of electrical devices attached thereto and said apparatus having a plurality of further electrical devices disposed-outside of said examination space and connected to said electrical devices on said patient support via cables, the improvement of a cable guide for said cables comprising:
a channel adapted to receive said cables disposed beneath said patient support and above said lower sub-antenna, said cable channel disposed at said wall of said examination space and having rounded edges projecting beyond the height of said lower sub-antenna said cable channel having a shape dependent on said polarized field.

2. In a nuclear magnetic resonance tomography apparatus having a magnet with a central opening defining an examination space and having a patient support movable into said examination space, said opening having a wall on which linearly polarizing whole-body antenna divided azimuthally into an upper sub-antenna and a lower sub-antenna is attached, said lower sub-antenna being disposed beneath said patient support when patient support is in said examination space, said patient support having a plurality of electrical devices attached thereto and said apparatus having further electrical devices disposed outside of said examination space and means for connecting said further electrical devices to said electrical devices on said patient support via cables, the improvement of a cable guide for said cables comprising:
a channel adapted to receive said cables disposed beneath said patient support and above said lower sub-antenna, said channel disposed at said wall of said opening and having a V-shape with a rounded edge facing said examination space, said edge projecting beyond the height of said lower sub-antenna.

3. The improvement of claim 2 wherein said means for connecting comprises a lower plug part disposed on said patient support and a connector unit in electrical connection with said lower plug part disposed beneath said patient support.

4. The improvement of claim 3 wherein said connector unit is disposed in said channel.

5. The improvement of claim 3 further comprising means for displacing said connector unit along said patient support together with said lower plug part.

6. The improvement of claim 3 wherein said connector unit contains a skin-effect wave barrier.

7. The improvement of claim 3 wherein said connector unit contains a directional coupler.

8. The improvement of claim 3 wherein said connector unit contains a preamplifier.

9. The improvement of claim 3 wherein said connector unit contains a signal converter.

10. In a nuclear magnetic resonance tomography apparatus having a magnet with a central opening defining an examination space and having a patient support movable into said examination space, said opening having a wall on which a circularly polarizing whole-body antenna is disposed, said whole-body antenna formed by a plurality of sub-antennas including a lower sub-antenna disposed beneath said patient support when said patient support is in said examination space, and neighboring sub-antennas respectively disposed at opposite ends of said lower sub-antenna, said patient support having a plurality of electrical devices attached thereto and said apparatus having further electrical devices disposed outside of said examination space and means for connecting said further electrical devices to said electrical devices on said patient support via cables, the improvement of a cable guide for said cables comprising:
a channel adapted to receive said cables disposed beneath said patient support and above said lower sub-antenna, said channel having approximately a U-shape and being disposed at said wall of said opening between one end of said lower sub-antenna and a neighboring sub-antenna, said channel having edges respectively rounded toward said lower sub-antenna and said neighboring sub-antenna, said edges projecting beyond the height of said lower sub-antenna and said neighboring sub-antenna.

11. The improvement of claim 10 wherein said means for connecting comprises a lower plug part disposed on said patient support and a connector unit in electrical connection with said lower plug part disposed beneath said patient support.

12. The improvement of claim 11 wherein said connector unit is disposed in said channel.

13. The improvement of claim 11 further comprising means for displacing said connector unit along said patient support together with said lower plug part.

14. The improvement of claim 11 wherein asid connector unit contains a skineffect wave barrier.

15. The improvement of claim 11 wherein said connector unit contains a directional coupler.

16. The improvement of claim 11 wherein said connector unit contains a preamplifier.

17. The improvement of claim 11 wherein said connector unit contains a signal converter.

* * * * *